United States Patent [19]

Mifune et al.

[11] 4,377,634

[45] Mar. 22, 1983

[54] METHOD FOR FORMING HIGH CONTRAST PHOTOGRAPHIC IMAGE

[75] Inventors: Hiroyuki Mifune; Shunji Takada; Yoshitaka Akimura; Yoshiharu Fuseya, all of Minami-ashigara, Japan

[73] Assignee: Fuji Photo Film Co., Ltd., Kanagawa, Japan

[21] Appl. No.: 129,458

[22] Filed: Mar. 11, 1980

Related U.S. Application Data

[63] Continuation-in-part of Ser. No. 939,616, Sep. 5, 1978, abandoned.

[30] Foreign Application Priority Data

Sep. 6, 1977 [JP] Japan .............................. 52-106885

[51] Int. Cl.$^3$ ................................................ G03C 5/30
[52] U.S. Cl. ..................................... 430/440; 430/441; 430/442; 430/446; 430/448; 430/611; 430/600; 430/599; 430/603; 430/564
[58] Field of Search ...................... 96/63, 66.3, 66, 95, 96/107, 109, 56; 430/440, 441, 442, 446, 448, 611, 600, 599, 603, 564

[56] References Cited

U.S. PATENT DOCUMENTS

| | | |
|---|---|---|
| 2,286,662 | 6/1942 | Weyde et al. |
| 2,419,975 | 5/1947 | Trirelli et al. |
| 2,732,300 | 1/1956 | Thirtle et al. |
| 3,227,552 | 1/1966 | Whitmore |
| 3,379,529 | 4/1968 | Porter et al. |
| 3,386,831 | 6/1968 | Honig et al. |
| 3,420,667 | 1/1969 | Copeland |
| 3,730,727 | 5/1973 | Olivares et al. |
| 3,782,949 | 1/1974 | Olivares et al. |
| 3,793,027 | 2/1974 | Okutsu et al. |
| 4,010,036 | 3/1977 | Suga et al. |

Primary Examiner—Won H. Louie, Jr.

Attorney, Agent, or Firm—Sughrue, Mion, Zinn, Macpeak and Seas

[57] ABSTRACT

A method for forming a high contrast negative photographic image, which comprises imagewise exposing a photographic material comprising a support having thereon at least one photographic silver halide emulsion layer with the photographic silver halide emulsion layer or at least one hydrophilic colloid layer of the photographic material containing a compound of the general formula (I)

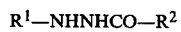

(I)

wherein $R^1$ represents an aryl group, and $R^2$ represents a hydrogen atom, a phenyl group, or an unsubstituted alkyl group containing 1 to 3 carbon atoms, and then developing the imagewise exposed material in the presence of a hydroquinone compound of the general formula (II)

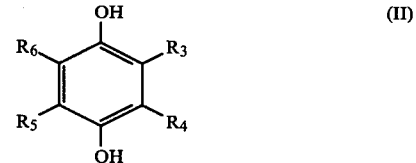

(II)

wherein $R^3$, $R^4$, $R^5$ and $R^6$, which may be the same or different, each represents a hydrogen atom, a sulfo group, an alkyl group, an aryl group, an aralkyl group, a heterocyclic group, or a group of the formula —O—$R^7$ or —S—$R^7$ where $R^7$ represents an alkyl group, an aryl group, an aralkyl group, or a heterocyclic group with at least one of $R^3$, $R^4$, $R^5$ and $R^6$ representing a group other than a hydrogen atom or a sulfo group.

12 Claims, No Drawings

METHOD FOR FORMING HIGH CONTRAST PHOTOGRAPHIC IMAGE

CROSS REFERENCE OF THE RELATED APPLICATION

This application is a continuation-in-part of application Ser. No. 939,616 filed Sept. 5, 1978, abandoned.

BACKGROUND OF THE INVENTION

1. Field of the Invention

This invention relates to a method for forming images, and particularly, to a method for forming very high contrast negative photographic images.

2. Description of the Prior Art

A method of obtaining photographic characteristics of a high contrast negative image by adding a hydrazine compound to a silver halide photographic emulsion is described in U.S. Pat. No. 2,419,975. U.S. Pat. No. 2,419,975 discloses that extremely high contrast photographic characteristics, such as a gamma ($\gamma$) of more than 10, can be obtained by adding a hydrazine compound to a silver chlorobromide emulsion and developing the emulsion with a developer having a pH as high as 12.8. However, strongly alkaline developers having a pH near 13 are so unstable that they tend to be oxidized by air and, therefore, cannot be used or stored for long periods of time. Moreover, development at such a high pH tends to cause fog to occur.

U.S. Pat. No. 3,386,831 describes a process for stabilizing an emulsion by adding a mono-phenylhydrazide of an aliphatic carboxylic acid to an essentially surface-sensitive photographic silver halide emulsion. The object and effect of the invention disclosed in U.S. Pat. No. 3,386,831 are to stabilize the emulsion, and differ from the objects and effect of the present invention.

Ultra-high-contrast photographic characteristics, either of a negative image or of a positive image, are very useful for the photographic reproduction of an image of a continuous tone comprising a dot image which is useful in making printing plates or the reproduction of a line image. For the above purposes, in the past a method of using a silver chlorobromide photographic emulsion having a silver chloride content of more than 50 mol%, preferably more than 75 mol%, and developing the emulsion with a hydroquinone developer having an extremely reduced effective concentration of sulfite ions (usually less than 0.1 mol/l) has been generally employed. However, in this method, since the concentration of the sulfite ion in the developer is low, the developer is very unstable and cannot be stored for a period exceeding 3 days. Furthermore, since a silver chlorobromide emulsion containing a relatively high percentage of silver chloride must be used, high sensitivity cannot be obtained.

Accordingly, use of an emulsion of high sensitivity and a stable developer to obtain ultra-high-contrast photographic characteristics useful for the reproduction of a dot image or a line image have been strongly desired.

SUMMARY OF THE INVENTION

A first object of this invention is to provide a method for forming an extremely high contrast negative photographic image using a stable developer.

A second object of this invention is to provide a method for forming a highly sensitive, extremely high contrast negative photographic image.

A further object of this invention is to provide a method for forming an extremely high contrast negative photographic image with a reduced amount of fog occurring.

The above objects of the present invention can be achieved by imagewise exposing a photographic material comprising a support having thereon at least one photographic silver halide emulsion layer containing silver halide grains and capable of providing a negative image, with the silver halide emulsion layer or at least one hydrophilic colloid layer of the photographic material containing a compound of the general formula (I)

$$R^1-NHNHCO-R^2 \qquad (I)$$

wherein $R^1$ represents an aryl group, and $R^2$ represents a hydrogen atom, a phenyl group, or an unsubstituted alkyl group with 1 to 3 carbon atoms, and then developing the exposed material in the presence of a hydroquinone derivative of the general formula (II)

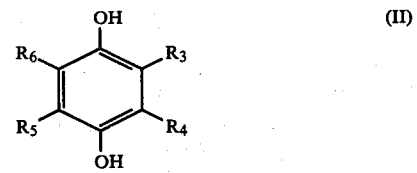

wherein $R^3$, $R^4$, $R^5$ and $R^6$, which may be the same or different, each represents a hydrogen atom, a sulfo group, an alkyl group, an aryl group, an aralkyl group, a heterocyclic group, or a group of the formula $-O-R^7$ or $-S-R^7$ where $R^7$ represents an alkyl group, an aryl group, an aralkyl group, or a heterocyclic group; with at least one of $R^3$, $R^4$, $R^5$ and $R^6$ representing a group other than a hydrogen atom or a sulfo group.

DETAILED DESCRIPTION OF THE INVENTION

It has already been found, as disclosed in U.S. Pat. Application Ser. Nos. 804,484 filed June 7, 1977, abandoned and 823,881 filed Aug. 11, 1977, U.S. Pat. No. 4,168,977 issued Sept. 25, 1979, (Corresponding to German Patent Applications Nos. (OLS) 2,725,743 and 2,736,229, respectively) that the above objects of this invention can be achieved to some extent by imagewise exposing a photographic material having at least one photographic silver halide emulsion layer consisting of silver halide grains having an average grain size of not more than 0.7 micron and being substantially of the surfae latent image type and containing not more than 250 g, per mole of silver halide, of a binder, with the emulsion layer or a hydrophilic colloid layer of the photographic material containing an organic acid hydrazide compound having a specified structure; and then developing the exposed material with a developer containing at least 0.15 mole/liter of a sulfite ion at a pH of about 11.0 to about 12.3. A new method which can be used to produce a highly sensitive, very high contrast photographic image by using a stable developer with improved results has now been found.

In the general formula (I) above, $R^1$ represents a monocyclic or bicyclic aryl group. A suitable example of a monocyclic aryl group for $R^1$ is a phenyl group and a suitable example of a bicyclic aryl group for $R^1$ is a naphthyl group. The aryl group may be unsubstituted or substituted with one or more substituents which are not electron-attracting, such as alkyl groups having 1 to 20 carbon atoms (which may be straight or branched chained e.g., methyl, ethyl, propyl, isopropyl, n-butyl, isobutyl, n-octyl, n-hexyl, tert-octyl, n-decyl, n-dodecyl, etc.), aralkyl groups having 1 to 3 carbon atoms in the alkyl moiety thereof (e.g., benzyl phenethyl, etc.), alkoxy groups having 1 to 20 carbon atoms (in which the alkyl moiety may be straight or branched chain, e.g., methoxy, ethoxy, 2-methylpropyloxy, etc.), amino groups which are mono- or disubstituted with alkyl groups having 1 to 20 carbon atoms (which may be straight or branched chain), aliphatic acylamino groups having 2 to 21 carbon atoms (in the acyl moiety) or aromatic acylamino groups (e.g., acetylamino. octynylamino, benzoylamino, dimethylamino, etc.), etc.

$R^2$ represents a hydrogen atom, an unsubstituted alkyl group having 1 to 3 carbon atoms which may be straight or branched chained (e.g., methyl, ethyl, n-propyl and isopropyl) or a phenyl group. The phenyl group may be unsubstituted or substituted with one or more substituents which preferably are electron-attracting groups, such as a halogen atom (chlorine or bromine, etc.), a cyano group, a trifluoromethyl group a carboxyl group or a sulfo group, etc.

Specific examples of suitable substituents represented by $R^1$ are a phenyl group, an α-naphthyl group, a β-naphthyl group, a p-tolyl group, an m-tolyl group, an o-tolyl group, a p-methoxyphenyl group, an m-methoxyphenyl group, a p-dimethylaminophenyl group, a p-diethylaminophenyl group, a p-(acetylamino)phenyl group, a p-(capryloylamino)phenyl group, a p-(benzoylamino)phenyl group and a p-benzylphenyl group.

Specific examples of suitable substituents represented by $R^2$, other than a hydrogen atom, are a methyl group, an ethyl group, an n-propyl group, an isopropyl group, a phenyl group, a 4-chlorophenyl group, a 4-bromophenyl group, a 3-chlorophenyl group, a 4-cyanophenyl group, a 4-carboxyphenyl group, a 4-sulfophenyl group, a 3,5-dichlorophenyl group and a 2,5-dichlorophenyl group.

The substituent represented by $R^1$ is preferably a monocyclic aryl group, and an unsubstituted phenyl group and a tolyl group are particularly preferred for $R^1$.

The substituent represented by $R^2$ is preferably a hydrogen atom, a methyl group or a phenyl group which may be substituted (e.g., with substituents as described above). A hydrogen atom is particularly preferred for $R^2$.

Of the compounds of the general formula (I), those of the general formula (Ia) are preferred.

$$R^1NHNHCOR^{12} \tag{Ia}$$

wherein $R^1$ is the same as defined with respect to the general formula (I), and $R^{12}$ represents a hydrogen atom, a methyl group, an unsubstituted phenyl group, or a phenyl group substituted with an electron-attracting group (e.g., as described above).

Of the compounds of the above general formula (Ia), the compounds represented by the following general formula (Ib) are preferred.

$$R^{11}NHNHCHO \tag{Ib}$$

In the above formula, $R^{11}$ represents an unsubstituted phenyl group or a tolyl group.

Specific examples of compounds represented by the general formula (I) are given below, but this invention is not to be construed as being limited thereto.

 (I-1)

 (I-2)

 (I-3)

 (I-4)

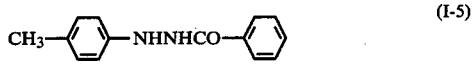 (I-5)

 (I-6)

 (I-7)

 (I-8)

 (I-9)

 (I-10)

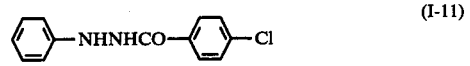 (I-11)

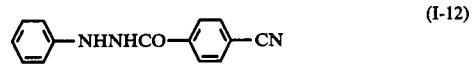 (I-12)

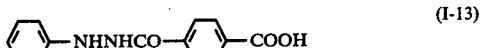 (I-13)

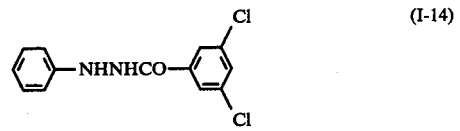 (I-14)

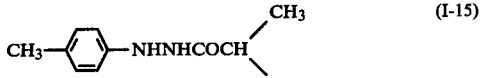 (I-15)

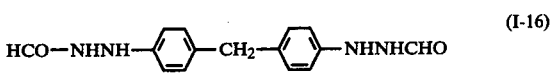 (I-16)

 (I-17)

  (I-18)

The compounds represented by the general formula (I) can be synthesized by reacting hydrazines with formic acid or by reacting hydrazines with acyl halides. Starting hydrazines such as

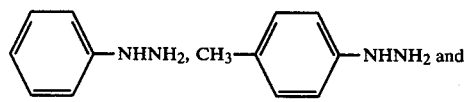

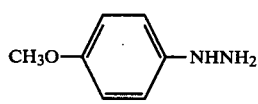

are commercially available and hydrazines of the formula

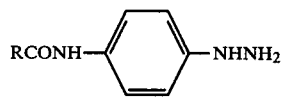

where R represents an alkyl group can be synthesized by reduction of a p-nitrophenylhydrazine. Suitable acyl halides which can be used include aliphatic acyl halides such as acetyl chloride, propionyl chloride, butyryl chloride, etc., and aromatic acyl halides such as benzoyl chloride, toluoyl chloride, etc. The reaction can be conducted in a solvent such as benzene, chloroform, pyridine, triethylamine, etc., and at a temperature of about 0° C. to about 100° C., preferably 0° C. to 70° C. A suitable molar ratio of the hydrazine to the acyl halide in the presence of a base such as pyridine or triethylamine which acts as a hydrogen halide acceptor for the hydrogen halide formed as a by-product ranges from about 1:1 to about 1:3, preferably 1:1.2 to 1:1.5 and in the absence of such a base ranges from about 1:0.3 to about 1:1, preferably 1:0.45 to 1:0.5. Hydrogen halide accepting agents such as triethylamine and pyridine can be employed in an amount of about 1 mol or more per mol of the acyl halide used.

Specific examples of the synthesis of the compounds of the general formula (I) are set forth below. Unless otherwise indicated herein, all parts, percents, ratios and the like are by weight.

SYNTHESIS EXAMPLE I

Synthesis of Compound (I-2)

110 g of formic acid was stirred at 25° to 30° C., and to this, 107 g of p-tolylhydrazine was gradually added. After completing the addition, heating was performed at 50° C. for 20 minutes while stirring the mixture. After cooling the mixture with ice, the resulting crystals were filtered out and recrystalized from 550 ml of acetonitrile to obtain 54.5 g of colorless needles having a melting point of 176° to 177° C.

SYNTHESIS EXAMPLE II

Synthesis of Compound (I-5)

15 g of p-tolylhydrazine was added to 100 ml of acetonitrile at 25° to 30° C. while stirring. Then, 15 g of benzoyl chloride was added dropwise at 25° to 30° C. After completing the addition, stirring was continued at 25° to 30° C. for 6 hours. After cooling the mixture with ice, the resulting crystals were filtered out and then recrystallized from benzene to obtain 7 g of colorless needles having a melting point of 146° C.

The amount of the compound of the general formula (I) present in the photographic material used in this invention is usually about $10^{-6}$ to $10^{-1}$ mole/mole Ag, preferably $2\times10^{-5}$ to $5\times10^{-2}$ mole/mole Ag. The compound of the general formula (I) can be incorporated in the emulsion by conventional methods used to incorporate additives into photographic emulsions. For example, a water-soluble compound can be dissolved in water to prepare an aqueous solution of a suitable concentration, and a water-insoluble or slightly water-soluble compound can be dissolved in a suitable water-miscible organic solvent such as alcohols (e.g., methanol, or ethanol), glycols (e.g., diethylene glycol, or triethylene glycol), ketones (e.g., acetone, or methyl ethyl ketone), esters (e.g., ethyl acetate) or amides (e.g., dimethylformamide) which do not adversely affect the photographic characteristics. The solution obtained is then added to the emulsion. Alternatively, a well-known method for adding a water-insoluble (or oil-soluble) coupler in the form of a dispersion to emulsions can also be used.

In the general formula (II) each of $R^3$, $R^4$, $R^5$ and $R^6$ represents a hydrogen atom, a sulfo group, a straight-chain or branched-chain alkyl group having 1 to 20 carbon atoms (e.g., methyl, ethyl, n-propyl, iso-propyl, n-butyl, tert-butyl, n-octyl, t-octyl, n-hexyl, n-dodecyl, n-hexadecyl, or n-octadecyl), an aryl group (e.g., a mono- or bicyclic aryl group such as phenyl or naphthyl), an aralkyl group (e.g., benzyl or phenethyl), a heterocyclic group (e.g., a 3-, 5- or 6-membered heterocyclic group containing one or more of a nitrogen atom, a sulfur atom, an oxygen atom and a selenium atom as hetero atoms such as benzotriazolyl, aziridinyl, or chromanyl), or a group of the formula -S-$R^7$ or -O-$R^7$. $R^7$ represents a straight-chain or branched-chain alkyl group having 1 to 20 carbon atoms (e.g., methyl, ethyl, n-propyl, iso-propyl, n-butyl, tert-butyl, n-octyl, t-octyl, n-hexyl, n-dodecyl, n-hexadecyl, or n-octadecyl), an aryl group (e.g., a mono- or bicyclic aryl group such as phenyl or naphthyl), an aralkyl group (e.g., benzyl or phenethyl), or a heterocyclic group (e.g., a 3-, 5- or 6-membered heterocyclic group containing one or more of a nitrogen atom, a sulfur atom, an oxygen atom and a selenium atom as hetero atoms such as thiazolyl, benzothiazolyl, imidazolyl, benzimidazolyl, tetrazolyl, thiadiazolyl, oxazolyl, benzoxazolyl, pyridyl, pyrimidyl, or tetrazaindenyl).

These groups for $R^3$, $R^4$, $R^5$, $R^6$ and $R^7$ can be unsubstituted or substituted with one or more of a sulfo group, a carboxyl group, a cyano group, a hydroxyl group, an amino group, a halogen atom (e.g., chlorine, bromine, or fluorine), an alkoxy group having 1 to 6 carbon atoms (e.g., methoxy, ethoxy, or propoxy), an alkoxycarbonyl group having 2 to 6 carbon atoms (e.g., methoxycarbonyl or ethoxycarbonyl), an acyloxy group having 2 to 6 carbon atoms (e.g., acetoxy or butyryloxy), an acylamino group having 2 to 6 carbon atoms (e.g., acetylamino or butyrylamino), an acyl group having 2 to 10 carbon atoms (e.g., acetyl, propionyl, valeryl, benzoyl, or toluoyl), an alkenyl group having 2 to 6 carbon atoms (e.g., allyl, 1-propenyl, 2-butenyl), an aralkyl group (e.g., benzyl or phenethyl), or an aryl group (e.g., phenyl, naphthyl, or tolyl). At least one of $R^3$, $R^4$, $R^5$ and $R^6$ represents a group other than a hydrogen atom or a sulfo group.

Preferred compounds of general formula (II) are those in which at least one of $R^3$, $R^4$, $R^5$ and $R^6$ represents an alkyl group, or a group of the formula $-O-R^7$ or $-S-R^7$. Especially preferred compounds of general formula (II) are those in which at least one of $R^3$, $R^4$, $R^5$ and $R^6$ is a group of the formula $-S-R^7$. $R^7$ represents a substituted or unsubstituted alkyl group, a substituted or unsubstituted aryl group, a substituted or unsubstituted aralkyl group, or a substituted or unsubstituted heterocyclic group. Of the substituents represented by $R^7$, heterocyclic groups and alkyl groups are preferred. Heterocyclic groups are especially preferred for $R^7$.

Especially preferred heterocyclic groups represented by $R^7$ are triazolyl, benzotriazolyl, tetrazolyl, phenyltetrazolyl, thiadiazolyl, and tetrazaindenyl groups.

Specific examples of the compound of the general formula (II) are given below. The invention should not be construed as being limited thereto, however (II-1): 2-Methyl-5-(1,1-dimethylbutyl)hydroquinone
(II-2): 2-p-Tolylhydroquinone
(II-3): 5-n-Dodecylthio-2-(1-phenyltetrazol-5-yl)thio-3-phenylthiohydroquinone
(II-4): 3-Phenylthio-5-n-octadecylthio-2-(1-phenyltetrazol-5-yl)-thiohydroquinone
(II-5): 2-Dodecylthio-5-(3-phenyl-1,3,4-thiadiazoline-2-thion-5-yl)thiohydroquinone
(II-6): 2-(3-Methylbutyl)hydroquinone
(II-7): 2-(1-Phenyltetrazol-5-yl)thio-5-octadecylthiohydroquinone
(II-8): 2-n-Pentadecyl-5-(1-phenyltetrazol-5-yl)-thiohydroquinone
(II-9): 2-(1Hydroxy-tetradecyl)hydroquinone
(II-10): 2-n-Hexadecyl-5-(2-methylthio-1,3,4-thiadiazol-5-yl)-thio-3-phenylthiohydroquinone,
(II-11): 2-Methyl-5-(1-phenyltetrazol-5-yl)thiohydroquinone
(II-12): 2-tert-Octyl-5-(2-methylthio-1,3,4-thiadiazol-5-yl)thiohydroquinone
(II-13): 2-(5-Methylbenzotriazol-2-yl)hydroquinone
(II-14): 2-(3-Phenyl-1,3,4-thiadiazoline-2-thion-5-yl)thio-5-(1,1,3,3-tetramethylbutyl)hydroquinone
(II-15): 2-Methoxy-5-(1-phenyltetrazol-5-yl)thiohydroquinone
(II-16): 2-(6-Methyl-1,3,3a,7-tetrazainden-4-yl)thio-6-(1,1,3,3-tetramethylbutyl)hydroquinone
(II-17): 2-(5-(n)-Pentyl-4-phenyl-1,2,4-triazol-3-yl)thio-5-(1,1,3,3-tetramethylbutyl)hydroquinone
(II-18): 2-Dodecylthiohydroquinone
(II-19): (1-Phenyl-tetrazol-5-yl)thiohydroquinone
(II-20): 2-(4,6-Dimethylbenzotriazol-2-yl)hydroquinone
(II-21): 2-n-Propylthiohydroquinone
(II-22): 2-(1-Phenyltetrazol-5-yl)thio-3-thiophenyl-5-(1,1,3,3-tetramethylbutyl)hydroquinone
(II-23): 2-(p-Methoxyphenyl)hydroquinone
(II-24): 2-Methoxyhydroquinone
(II-25): 2-n-Octadecylhydroquinone
(II-26): 2,5-bis-(1,1,3,3-Tetramethylbutyl)hydroquinone
(II-27): 2-n-Dodecylhydroquinone
(II-28): Tetramethylhydroquinone
(II-29): 2-n-Octylhydroquinone
(II-30): 2-(1,1,3,3-Tetramethylbutyl)-5-(2-carboxyphenylthio)hydroquinone
(II-31): 2-(1,1,3,3-tetramethylbutyl)-5-n-dodecylthiohydroquinone
(II-32): 2,5-bis-(Dimethylaminomethyl)hydroquinone
(II-33): 2-(1,1,3,3-Tetramethylbutyl)-5-phenylhydroquinone
(II-34): 2-(3-Hydroxyphenoxy)hydroquinone
(II-35): 2,5-Dibenzyloxyhydroquinone
(II-36): 2,3,5-Trimethyl-6-(n-dodecylthio)hydroquinone
(II-37): 2-(1,1,3,3-Tetramethylbutyl)-5-(1-phenylpropyl)hydroquinone
(II-38): Sodium 2-n-pentadecylhydroquinone-5-sulfonate,
(II-39): Sodium 2-n-pentadecylthiohydroquinone-5-sulfonate The compounds of the general formula (II) used in this invention can be prepared, for example, in accordance with the disclosures in U.S. Pat. Nos. 2,008,032, 2,008,337, 2,732,300, and 3,379,529, Japanese Patent Application (OPI) Nos. 129536/74 and 93971/75 (The term "OPI" as used herein refers to a "published unexamined Japanese patent application"), E. C. Armstrong et al., *J. Am. Chem. Soc.*, 82, 1928–1935 (1960), D. E. Koalens, *J. Am. Chem. Soc.* 56, 2478–2481 (1934), and *Journal of the Japanese Pharmaceutical Society*, 56, 814–828 (1936).

Specific methods for synthesizing some of the above compounds are described below.

SYNTHESIS EXAMPLE III

Synthesis of Compound (II-17)

13 g of 3-mercapto-5-n-pentyl-4-phenyl-1,2,4-triazole was dissolved in 200 ml of methanol, and the solution was stirred under ice cooling. To the solution was added 12 g of 2-(1,1,3,3-tetramethylbutyl)benzoquinone in small portions. After the addition, the solution was stirred under ice cooling for 2 hours, and then allowed to stand at room temperature (25°±5° C.) overnight. The methanol was removed under reduced pressure, and 20 ml of diethyl ether was added to the residue. The crystals obtained were collected by filtration, and recrystallized from ethyl acetate to obtain 5 g of 2-(5-n-pentyl-4-phenyl-1,2,4-triazol-3-ylthio)-5-(1,1,3,3-tetramethylbutyl)hydroquinone having a melting point of 198° C.

SYNTHESIS EXAMPLE IV

Synthesis of Compound (II-18)

20 g of dodecyl mercaptan was dissolved in 200 ml of methanol, and 11 g of p-benzoquinone was added thereto. The mixture was stirred at room temperature, allowed to stand overnight, and then concentrated under reduced pressure. 250 ml of ethyl acetate and 11 g of diethylhydroxyamine were added to the residue, and the mixture was heated under reflux for 4 hours. The product was cooled, washed with 100 ml of a 0.1 N hydrochloric acid aqueous solution, dried over sodium sulfate, and concentrated under reduced pressure. Recrystallization of the residue from benzene gave 20 g of 2-dodecylthiohydroquinone having a melting point of 75° to 76° C.

SYNTHESIS EXAMPLE V

Synthesis of Compound (II-5)

17 g of 2-dodecylthiobenzoquinone was dissolved in 400 ml of methanol, and 17 g of 5-mercapto-3-phenyl-1,3,4-thiadiazoline-2-thione was added thereto. The mixture was heated under reflux for 2 hours. The methanol was evaporated off, and the residual oily material was crystallized by addition of a benzene-hexane mixture (1:2 by vol). The crystals were collected by filtration, and recrystallized from methanol to obtain 7 g of 2-dodecylthio-5-(3-phenyl-1,3,4-thiadiazoline-2-thion-2-yl)thiohydroquinone having a melting point of 122° to 123° C.

SYNTHESIS EXAMPLE VI

Synthesis of Compound (II-3)

200 ml of methanol was added to 15.4 g of 2-dodecylthiobenzoquinone and 8.9 g of 5-mercapto-1-phenyltetrazole, and the mixture was heated under reflux for 2 hours. The methanol was evaporated off, and the residue was recrystallized from hexane to obtain 19 g of 2-dodecylthio-5-(1-phenyltetrazol-5-yl)hydroquinone. To the product were added 200 ml of benzene and 20 g of manganese oxide, and the mixture was heated under reflux for 4 hours. The manganese oxide and other insoluble materials were removed by filtration while hot, and the filtrate was cooled. The crystals precipitated (15 g) were collected by filtration. 100 ml of methanol and 3.4 g of thiophenol were added, and the mixture was stirred at 40° C. for 4 hours and then allowed to stand overnight at room temperature. The methanol was evaporated off. Recrystallization of the resulting crystals from a benzene-hexane mixture (1:2 by vol) gave 8 g of 2-(1-phenyltetrazol-5-yl)-thio-3-phenylthio-5-dodecylthiohydroquinone having a melting point of 107° to 108° C.

SYNTHESIS EXAMPLE VII

Synthesis of Compound (II-13)

400 ml of water and 200 ml of conc. hydrochloric acid (12 N) were added to 52 g of 3-nitro-p-toluidine, and under ice cooling (at less than 5° C.), an aqueous solution (containing 100 ml of water) of 28 g of sodium nitrite was added dropwise thereto. The mixture was then added to a mixed aqueous solution (containing 2 liters of water) of 212 g of sodium carbonate, 18 g of sodium hydroxide and 52 g of 4-methylphenol under ice cooling (at less than 10° C.). After standing overnight, the crystals precipitated were collected by filtration. 500 ml of methanol, 200 of a 40% aqueous solution of sodium hydroxide and 120 g of zinc were added to the crystals (115 g), and the mixture was heated for 4 hours over a hot water bath. The product was filtered to remove the zinc. The methanol was evaporated off from the filtrate, and the residue was acidified with hydrochloric acid to obtain crystals. The crystals were purified by recrystallization from methanol. To the crystals (35 g) were added 320 ml of acetic acid and 210 ml of hydrobromic acid, and the mixture was heated at 160° C. for 3 hours. The product was cooled and the precipitated crystals were collected by filtration, and recrystallized from an ethanol-water mixture (1:1 by vol) to afford 20 g of 4-methylbenzotriazol-2-ylhydroquinone having a melting point of 202° to 203° C.

The compound of the general formula (II) used in this invention may be incorporated into at least one silver halide photographic emulsion layer of the silver halide photographic material containing the compound of the general formula (I), or into a non-light-sensitive layer of the photographic material. Alternatively, the compound of the general formula (II) may be included in a developer used to process the silver halide photographic material containing the compound of general formula (I).

Alternatively, the photographic material containing the compound of the general formula (I), after exposure, can be treated with a bath containing the compound of the general formula (II) before the photographic material is developed.

When the compound of the general formula (II) is employed in a photographic silver halide emulsion, a suitable amount is usually about $5 \times 10^{-7}$ to $5 \times 10^{-2}$ mole/mole Ag, preferably $5 \times 10^{-6}$ to $1 \times 10^{-2}$ mole/mole Ag. When the compound of the general formula (II) is employed in a non-light-sensitive layer of the photographic material, a suitable amount is as described above based on the silver halide in the adjacent silver halide emulsion layer. When the compound of general formula (II) is employed in a developer, a suitable amount is about $10^{-7}$ to $10^{-2}$ mole, preferably $3 \times 10^{-6}$ to $3 \times 10^{-3}$ mole, per liter of the developer.

The compound of the general formula (II) can be added to a silver halide emulsion or a layer adjacent thereto using any conventional method of incorporating additives into photographic emulsions. For example, a water-soluble compound can be dissolved in water in a suitable concentration, and a water-insoluble or slightly water-soluble compound can be dissolved in a suitable mater-miscible organic solvent, such as alcohols, ethers, glycols, ketones, esters, or amides which do not adversely affect the photographic characteristics. The solution is then added to the emulsion. Well-known methods used to add a water-insoluble (or oil-soluble) coupler in the form of a dispersion to an emulsion can also be used.

The compound of the general formula (I) or (II) may be added to a photographic silver halide emulsion at any desired time from the beginning of chemical ripening to just before coating. Preferably, the addition is made just after chemical ripening of the silver halide emulsion. Addition of the compound to a coating composition prepared for coating is especially preferred. When the compound of the general formula (I) and the compound of the general formula (II) are to be added to layers of the photographic material, they may be added to the same layer or to separate layers. There is no particular restriction on the order of adding the compounds of the general formulae (I) and (II).

The compound of the general formula (II) may be added as a solution in water or a water-miscible organic solvent such as alcohols (e.g., methanol, or ethanol), ketones (e.g., acetone, or methyl ethyl ketone), or esters (e.g., ethyl acetate) during the preparation of a developer or to a prepared developer. The solvent may, if desired, be alkaline or acidic.

By using the compounds of the general formulae (I) and (II) in combination, a highly sensitive and very high contrast negative photographic image can be obtained. Even when the compound of general formula is used in a small amount, very high contrast, negative photographic images can be obtained.

Silver halide grains which are present in the silver halide emulsion layer used in this invention are preferably substantially surface layent image type silver halide grains. The expression "substantially surface latent image type" silver halide grains as used in this specification means that the sensitivity obtained by (A) surface development is higher than that obtained by (B) internal development when development is carried out by (A) a surface development method and (B) an internal development method described below after exposure to light for 1 to 1/100 second. The sensitivity as used herein is defined as follows:

$$S = (100/Eh)$$

wherein S is the sensitivity, and Eh is the exposure amount required to obtain a density just intermediate between the maximum density (Dmax) and the minimum density (Dmin), i.e., ½(Dmax+Dmin).

(A) Surface Development

Development is carried out at a temperature of 20° C. for 10 minutes in a developer of the following formulation.

| N-Methyl-p-aminophenol (hemisulfate) | 2.5 g |
|---|---|
| Ascorbic Acid | 10 g |
| Sodium Metaborate (tetrahydrate) | 35 g |
| Potassium Bromide | 1 g |
| Water to make | 1 l |

(B) Internal Development

After treatment at about 20° C. for 10 minutes in a bleaching solution containing 3 g/l of ferricyanide and 0.0125 g/l of phenosafranine and then washing for 10 minutes, development is carried out at 20° C. for 10 minutes in a developer of the following formulation.

| N—Methyl-p-aminophenol (hemisulfate) | 2.5 g |
|---|---|
| Ascorbic Acid | 10 g |
| Sodium Metaborate (tetrahydrate) | 35 g |
| Potassium Bromide | 1 g |
| Sodium Thiosulfate | 3 g |
| Water to make | 1 l |

The silver halide may be silver chloride, silver chlorobromide, silver iodochlorobromide, silver bromide, and silver iodochloride. In the case of silver chlorobromide or silver iodochlorobromide, the silver chloride content is preferably about 80 mole% or less. In the case of silver iodobromide or silver iodochlorobromide, the silver iodide content preferably does not exceed 10 mole%. Especially preferably, the silver chloride content does not exceed 50 mole%, and the silver iodide content does not exceed 6 mole%.

Since such a broad range of silver halides can be used in the process of this invention, far higher sensitivity than in conventional methods using "lith" type development can be obtained.

The photographic emulsion used in this invention can be prepared using the methods described in, e.g., P. Glafkides, *Chimie et Physique Photographique*, Paul Montel, Paris (1967), G. F. Duffin, *Photographic Emulsion Chemistry*, The Focal Press, London (1966), V. L. Zelikman et al., *Making and Coating Photographic Emulsions*, The Focal Press, London (1964), etc. That is, any of the acid method, the neutral method, the ammonia method and other methods can be used. Moreover, the reaction of a soluble silver salt with a soluble halogen salt can be accomplished using any of the single jet method, the double jet method and a combination thereof.

The method in which grains are formed in the presence of an excess of silver ions (the so-called reverse mixing method) can also be used. As one of the modes of the double jet method, the method in which the pAg of the liquid phase in which the silver halide is to be produced is kept constant, that is, the so-called controlled double jet method, can be used. This method can provide silver halide emulsions having a regular crystal form and an almost uniform grain size.

The silver halide grains in the photographic emulsion used in this invention can have a relatively wide grain size distribution, but a narrow grain size distribution is preferred. In particular, the size of the silver halide grains amounting to 90% of the total, based on the weight or number of the grains, is preferably within ±40% of the average grain size (such an emulsion is usually called a monodispersed emulsion).

The average grain size of the silver halide grains is preferably not more than about $0.7\mu$. The term "average grain size" is commonly used by those skilled in the art of silver halide photography and is well understood. The term "grain size" means the diameter of the grains when the grains are spherical or approximate spheres. With cubic grains, the grain size refers to the length of an edge$\times\sqrt{4/\pi}$. The average grain size is determined as an algebraic average or geometric average based on the projected area of the grains. Details of the measurement of the average grain size are described in C. E. K. Mees & T. H. James, *The Theory of the Photographic Process*, 3rd Ed., pp. 36–43, Macmillan, New York (1966).

The average grain size of the emulsion used in this invention is preferably not more than $0.4\mu$. Although the average grain size is small, the light-sensitive material used in this invention has high sensitivity characteristics.

The silver halide grains in the photographic emulsion may be regular crystals such as cubic crystals or octahedral crystals, or irregular crystals such as spherical crystals or plate-like crystals, or may have a composite crystal form of these crystal forms. The grains may comprise mixed grains having various crystal forms.

The interior and the surface layer of the silver halide grain may be different or the grains may be uniform throughout.

In the process of the formation of the silver halide grains or physical ripening, cadmium salts, zinc salts, lead salts, thallium salts, rhodium salts or complex salts thereof, iron salts or iron complex salts, and the like can be present.

Two or more of silver halide emulsions which are separately prepared can be mixed and then used, if desired.

Gelatin is advantageously used as a binder or protective colloid in the photographic emulsion, but other hydrophilic colloids can also be used. For example, gelatin derivatives, graft polymers of gelatin with other high molecular weight materials, proteins such as albumin or casein, cellulose derivatives such as hydroxyethyl cellulose, carboxymethyl cellulose or cellulose sulfate, saccharide derivatives such as sodium alginate or starch derivatives, various synthetic hydrophilic high molecular weight materials such as homopolymers or copolymers, e.g., polyvinyl alcohol, polyvinyl alcohol (partial acetal), poly-N-vinyl pyrrolidone, polyacrylic acid, polymethacrylic acid, polyacrylamide, polyvinyl imidazole, polyvinyl pyrazole, etc., can be used.

Lime-processed gelatin and acid-processed gelatin can be used as the gelatin. Also, gelatin which is hydrolyzed or which is decomposed by enzymes can be used. Suitable gelatin derivatives are those which are prepared by reacting gelatin with various compounds such as acid halides, acid anhydrides, isocyanates, bromoacetic acid, alkanesultones, vinylsulfonamides, maleinimide compounds, polyalkylene oxides or epoxy compounds. Specific examples of these gelatin derivatives are described in, e.g., U.S. Pat. Nos. 2,614,928, 3,132,945, 3,186,846 and 3,312,553, British Pat. Nos. 861,414, 1,033,189 and 1,005,784, Japanese Patent Publication 26,845/67, etc.

Examples of gelatin graft polymers include those prepared by grafting a homopolymer or a copolymer of a vinylic monomer such as acrylic acid, methacrylic acid, the derivatives thereof (such as the esters or the amides thereof), acrylonitrile or styrene to gelatin. In particular, graft polymers prepared from polymers which are compatible with gelatin to some degree, such as those of acrylic acid, methacrylic acid, acrylamide, methacrylamide or a hydroxyalkyl methacrylate are preferred. Examples of these polymers are described in, e.g., U.S. Pat. Nos. 2,763,625, 2,831,767 and 2,956,884, etc. Typical synthetic hydrophilic high molecular weight materials are described in, e.g., German Patent Application (OLS) 2,312,708, U.S. Pat. Nos. 3,620,751 and 3,879,205, Japanese Patent Publication No. 7,561/68, etc.

The silver halide emulsions of the present invention contain preferably not more than about 250 g of binder per mol of silver halide. If the emulsions contain a binder in an amount of not more than about 250 g per mol of silver halide, an extremely high contrast photographic characteristic of a $\gamma$ of more than about 10 which is an object of the present invention can be easily obtained.

After the formation of the precipitates or after physical ripening, the soluble salts are usually removed from the emulsion. For this purpose, the well known noodle washing method in which gelatin is subjected to gelation may be used. Furthermore, the flocculation method which employs an inorganic salt having a polyvalent anion such as sodium sulfate, an anionic surface active agent, an anionic polymer (such as polystyrene sulfonic acid) or a gelatin derivative (such as an aliphatic acylated gelatin, an aromatic acylated gelatin or an aromatic carbamoylated gelatin) may be used. The removal of the soluble salts may be omitted, if desired.

Although the silver halide emulsions used in the present invention do not need to be chemically sensitized, chemically sensitized silver halide emulsions are preferred. Processes for chemical sensitization of the silver halide emulsions which can be used include known sulfur sensitization, reduction sensitization and noble metal sensitization processes. These processes are described in references such as P. Glafkides, *Chimie et Physique Photographique,* Paul Montel, Paris (1967) or Zelikmann, *Making and Coating Photographic Emulsions,* The Focal Press, London (1964) or H. Frieser, *Die Gundlagen der photographischen Prozesse mit Silberhalogeniden,* Akademische Verlagsgesellschaft (1968). In the noble metal sensitization processes, a gold sensitization process is a typical process where gold compounds or mainly gold complexes are used.

Complexes of noble metals other than gold, such as those of platinum, palladium or iridium, etc. can also be used. A reduction sensitization process may be used if the process does not generate fog to a degree which causes practical difficulties. A particularly preferred chemical sensitization process for the present invention is the use of a sulfur sensitization process.

Examples of sulfur sensitizing agents which can be used include not only sulfur compounds present in the gelatin per se but also various sulfur compounds such as thiosulfates, thioureas, thiazoles or rhodanines, etc. Examples of suitable sulfur compounds are described in U.S. Pat. Nos. 1,574,994, 2,410,689, 2,278,947, 2,728,668 and 3,656,955. Typical examples of reduction sensitizing agents which can be used include stannous salts, amines, formamidine sulfinic acid and silane compounds, etc., as described in U.S. Pat. Nos. 2,487,850, 2,518,698, 2,983,609, 2,983,610 and 2,694,637. For noble metal sensitization, complex salts of the Group VIII metals such as gold, platinum, iridium or palladium can be used, and specific examples of these salts are described in, e.g., U.S. Pat. No. 2,448,060, British Pat. No. 618,061, etc.

The photographic material used in this invention may contain an anti-foggant. Examples of anti-foggants which can be advantageously used for the photographic material used in this invention are 1,2,4-triazole compounds substituted with a mercapto group at the 3-position, benzotriazole compounds, 2-mercaptobenzimidazole compounds (which do not contain a nitro group), 2-mercaptopyrimidines, 2-mercaptobenzothiazoles, benzothiazolium compounds (such as N-alkylbenzothiazolium halides, or N-allylbenzothiazolium halides), and 2-mercapto-1,3,4-thiazoles. Antifoggants which are not effective when used alone, such as 6-nitrobenzimidazole, however, can be used in combination with advantageous antifoggants.

The effect of this invention is enhanced even more by adding a small amount of an iodide (such as potassium iodide) to the emulsion after the formation of the grains, before chemical ripening; after chemical ripening or before coating. A suitable amount of iodide added ranges from about $10^{-4}$ to about $10^{-2}$ mol/mol Ag.

The photographic emulsions used in this invention can be spectrally sensitized with methine or other dyes. Suitable sensitizing dyes include cyanine dyes, merocyanine dyes, complex cyanine dyes, complex merocyanine dyes, holopolar cyanine dyes, hemicyanine dyes, styryl dyes and hemioxonol dyes. Particularly useful dyes are cyanine dyes, merocyanine dyes and complex merocyanine dyes. These dyes can contain, as a basic heterocyclic nucleus, any of the nuclei which are usually employed in cyanine dyes. That is, a pyrroline nucleus, an oxazoline nucleus, a thiazoline nucleus, a pyrrole nucleus, an oxazole nucleus, a thiazole nucleus, a selenazole nucleus, an imidazole nucleus, a tetrazole nucleus, a pyridine nucleus and the like; these nuclei described-above condensed with an alicyclic hydrocarbon ring; and these nuclei described-above condensed with an aromatic hydrocarbon ring, such as an indolenine nucleus, a benzindolenine nucleus, an indole nucleus, a benzoxazole nucleus, a naphthoxazole nucleus, a benzothiazole nucleus, a naphthothiazole nucleus, a benzoselenazole nucleus, a benzimidazole nucleus and a quinoline nucleus. The carbon atoms of the above-described nuclei may be substituted.

The merocyanine dyes or complex merocyanine dyes can contain, as a nucleus having a ketomethylene structure, a 5- to 6-membered heterocyclic nucleus such as a pyrazolin-5-one nucleus, a thiohydantoin nucleus, a 2-thiooxazolidin-2,4-dione nucleus, a thiazolidin-2,4-dione nucleus, a rhodanine nucleus or a thiobarbituric acid nucleus.

Useful sensitizing dyes are those described in, e.g., German Pat. No. 929,080, U.S. Pat. Nos. 2,231,658, 2,493,748, 2,503,776, 2,519,001, 2,912,329, 3,656,959, 3,672,897 and 3,694,217, British Pat. No. 1,242,588, Japanese Patent Publication No. 14,030/69, etc.

These sensitizing dyes may be used individually or as a combination thereof. A combination of sensitizing dyes is often employed particularly for the purpose of supersensitization. Typical examples of such combinations are described in, e.g., U.S. Pat. Nos. 2,688,545, 2,977,229, 3,397,060, 3,522,052, 3,527,641, 3,617,293, 3,628,964, 3,666,480, 3,679,428, 3,703,377, 3,769,301, 3,814,609 and 3,837,862, British Pat. No. 1,344,281, Japanese Patent Publication No. 4,936/68, etc.

The sensitizing dyes may be present in the emulsion together with dyes which themselves do not have any spectral sensitizing effects but exhibit a supersensitizing effect when used in combination or materials which do not substantially absorb visible light but exhibit a supersensitizing effect when used in combination. For example, aminostilbene compounds substituted with a nitrogen-containing heterocyclic ring group (e.g., those described in U.S. Pat. Nos. 2,933,390 and 3,635,721), aromatic organic acid formaldehyde condensates (e.g., those described in U.S. Pat. No. 3,743,510), azaindene compounds, and the like, can be present. The combinations described in U.S. Pat. Nos. 3,615,613, 3,615,641, 3,617,295 and 3,635,721 are particularly useful.

A water-soluble dye may be present in any of the hydrophilic colloid layers in the photographic light-sensitive material used in this invention as a filter dye or for prevention of light scattering, antihalation or various other purposes. Examples of these dyes include oxonol dyes, hemioxonol dyes, styryl dyes, merocyanine dyes, cyanine dyes and azo dyes. Of these dyes, oxonol dyes, hemioxonol dyes and merocyanine dyes are particularly useful. Specific examples of dyes which can be used are those described in British Pat. Nos. 584,609 and 1,177,429, Japanese Patent Application (OPI) Nos. 85,130/73, 99620/74 and 114,420/74, and U.S. Pat. Nos. 2,274,782, 2,533,472, 2,956,879, 3,148,187, 3,177,078, 3,247,127, 3,540,887, 3,575,704, 3,653,905 and 3,718,472.

An inorganic or organic hardener may be present in any of the hydrophilic colloid layers in the light-sensitive material used in this invention. For example, chromium salts (such as chrome alum or chromium acetate), aldehydes (such as formaldehyde, glyoxal or glutaraldehyde), N-methylol compounds (such as dimethylolurea or methyloldimethylhydantoin), dioxane derivatives (such as 2,3-dihydroxydioxane), active vinyl compounds (such as 1,3,5-triacryloyl-hexahydro-s-triazine or bis(vinylsulfonyl)methyl ether), active halogen compounds (such as 2,4-dichloro-6-hydroxy-s-triazine), mucohalic acids (such as mucochloric acid or mucophenoxychloric acid), isooxazoles, dialdehyde starch, 2-chloro-6-hydroxytriazinylated gelatin and the like can be used individually or in combination. Specific examples of these compounds are described in, e.g., U.S. Pat. Nos. 1,870,354, 2,080,019, 2,726,162, 2,870,013, 2,983,611, 2,992,109, 3,047,394, 3,057,723, 3,103,437, 3,321,313, 3,325,287, 3,362,827, 3,539,664 and 3,543,292, British Pat. Nos. 676,628, 825,544 and 1,270,578, German Pat. Nos. 872,153 and 1,090,427, Japanese Patent Publications Nos. 7,133/69 and 1,872/71, etc.

The light-sensitive material of this invention may contain various known surface active agents for various purposes, e.g., as a coating aid, for preventing the generation of static charges, improving slip characteristics, improving emulsion dispersion, preventing adhesion, improving photographic characteristics (e.g., accelerating development, increasing contrast, sensitization), etc.

For example, nonionic surface active agents such as saponin (steroids), alkylene oxide derivatives (such as polyethylene glycol, polyethylene glycol/polypropylene glycol condensates, polyethylene glycol alkyl or alkylaryl ethers, polyethylene glycol esters, polyethylene glycol sorbitan esters, polyalkylene glycol alkylamines or amides or silicone/polyethylene oxide adducts), glycidol derivatives (such as alkenylsuccinic acid polyglycerides or alkylphenol polyglycerides), aliphatic esters of polyhydric alcohols, alkyl esters of sucrose, urethanes or ethers; anionic surface active agents containing an acidic group such as a carboxy group, a sulfo group, a phospho group, a sulfuric acid ester group or a phosphoric acid ester group, such as triterpenoid type saponin, alkylcarboxylates, alkylsulfonates, alkylbenzenesulfonates, alkylnaphthalenesulfonates, alkyl sulfuric acid esters, alkyl phosphoric acid esters, N-acyl-N-alkyltaurines, sulfosuccinates, sulfoalkylpolyoxyethylene alkylphenyl ethers or polyoxyethylene alkylphosphates; amphoteric surface active agents such as amino acids, aminoalkylsulfonic acids, aminoalkylsulfuric acid esters, aminoalkylphosphoric acid esters, alkylbetaines, amineimides or amine oxides; and cationic surface active agents such as alkylamine salts, aliphatic or aromatic quaternary ammonium salts, (such as pyridinium or imidazolium salts) or phosphonium or sulfonium salts containing an aliphatic or heterocyclic ring can be used.

Specific examples of these surface active agents are those described in, e.g., U.S. Pat. Nos. 2,240,472, 2,831,766, 3,158,484, 3,210,191, 3,294,540 and 3,507,660, British Pat. Nos. 1,012,495, 1,022,878, 1,179,290 and 1,198,450, Japanese Patent Application (OPI) No. 117,414/75, U.S. Pat. Nos. 2,739,891, 2,823,123, 3,068,101, 3,415,649, 3,666,478 and 3,756,828, British Pat. No. 1,397,218, U.S. Pat. Nos. 3,133,816, 3,441,413, 3,475,174, 3,545,974, 3,726,683 and 3,843,368, Belgian Pat. No. 731,126, British Pat. Nos. 1,138,514, 1,159,825 and 1,374,780, Japanese Patent Publications Nos. 378/65, 379/65 and 13,822/68, U.S. Pat. Nos. 2,271,623, 2,288,226, 2,944,900, 3,253,919, 3,671,247, 3,772,021, 3,589,906 and 3,754,924, German Patent Application (OLS) No. 1,961,638, Japanese Patent Application (OPI) No. 59,025/75, etc.

The photographic emulsion used in this invention can contain a dispersion of a synthetic polymer which is insoluble or slightly soluble in water for the purpose of improving the dimensional stability, or other purposes. Examples of polymers which can be used include polymers composed of one or more alkyl acrylates or methacrylates, alkoxyalkyl acrylates or methacrylates, glycidyl acrylates or methacrylates, acryl or methacrylamide, vinyl esters (for example, vinyl acetate), acrylonitrile, olefins and styrene, etc., and polymers comprising a combination of the above-described monomers and acrylic acid, methacrylic acid, $\alpha,\beta$-unsaturated dicarboxylic acids, hydroxyalkyl acrylates or methacrylates or styrenesulfonic acid, etc. For example, those compounds described in U.S. Pat. Nos. 2,376,005, 2,739,137, 2,853,457, 3,062,674, 3,411,911, 3,488,708, 3,525,620, 3,607,290, 3,635,715 and 3,645,740, and British Pat. Nos. 1,186,699 and 1,307,373 can be used. A suitable amount of the polymer ranges from about 20 to 80% by weight based on the total weight of the binders. Since high contrast emulsions such as that used in this invention are suitable for the reproduction of line drawings and the dimensional stability is of importance for such a purpose, it is preferred for the above-described polymer dispersion to be employed.

The photographic emulsions are coated on conventional supports which do not undergo serious dimensional changes during processing. Typical supports which can be used are a cellulose acetate film, a polystyrene film, a polyethylene terephthalate film, a polycarbonate film, a laminate thereof, paper, baryta paper, paper coated or laminated with a hydrophobic polymer such as polyethylene, polypropylene, etc., as are commonly used for photographic light-sensitive materials. Transparent supports can be employed for certain end-uses of the light-sensitive material. Also, transparent supports may be colored by adding a dye or a pigment thereto as described in J. SMPTE, 67, 296 (1958), etc.

Where the adhesion between the support and the photographic emulsion layer(s) is insufficient, a subbing layer (an adhesive layer adhesive to both the support and the photographic emulsion layer(s) can be employed. Also, in order to improve the adhesion, the surface of the support may be subjected to a preliminary processing such as a corona discharge, an irradiation with ultraviolet light, a flame treatment, etc. A suitable coating amount of silver is about 0.5 g/m² to about 10 g/m² of the support.

Exposure to light for obtaining a photographic image can be performed in a conventional manner. Various known light sources such as natural light (sunlight), a tungsten lamp, a fluorescent light, a mercury lamp, a xenon arc lamp, a carbon arc lamp, a xenon flash lamp or a cathode ray tube flying spot can be used. The exposure time can, of course, be about 1/1,000 sec to about 1 sec which is usually employed with cameras, and further, exposure for shorter than about 1/1,000 sec, for example, about $1/10^4$ to about $1/10^6$ sec which is employed in case of using a xenon flash lamp or a cathode ray tube, and exposure for longer than about 1 sec can be employed. If desired, the spectral composition of the light used for the exposure can be controlled using a color filter. The fluorescence resulting from the excitation of a phosphor caused by ionizing radiation or a laser beam can also be used for exposure. Moreover, exposure to electron beams, X-rays, γ-rays or α-rays may be employed.

The photographic light-sensitive material of this invention can be photographically processed using known methods and known processing solutions. The processing temperature usually ranges from about 18° to about 50° C., but temperatures lower than about 18° C. or higher than about 50° C. may be used. This invention is useful for the formation of an image by development in which a silver image is formed (a black-and-white photographic processing).

The developers used for black-and-white photographic processing preferably contain, as a developing agent, aminophenols (such as N-methyl-p-aminophenol), 3-pyrazolidones (such as 1-phenyl-3-pyrazolidone), 1-phenyl-3-pyrazolines, dihydroxybenzenes (such as hydroquinone), and combinations of a dihydroxybenzene (such as hydroquinone) and other of the afore-mentioned developing agents. Specific examples of the useful developing agents include hydroquinone alone, hydroquinone plus N-methyl-p-aminophenol, hydroquinone plus 1-phenyl-3-pyrazolidone, and hydroquinone plus N-methyl-p-aminophenol plus 1-phenyl-3-pyrazolidone. Moreover, the developers usually contain a known antioxidant, an alkali agent, a pH buffer or the like and, if desired, a dissolving aid, a color toning agent, a development accelerator, a surface active agent, an anti-foaming agent, a water softener, a hardener, a tackifier, etc., may be present. An anti-fogging agent (such as an alkali metal halide or benzotriazole) may be present in the developer.

According to this invention, even when development is carried out using a developer containing more than about 0.15 mol/l of sulfite ions, a γ of more than 8 can be obtained. The pH of the developer is preferably about 11 to about 12.3. If the pH exceeds about 12.3, the developer is unstable even when a high concentration of sulfite ions is present, and it is difficult to maintain stable photographic characteristics for more than 3 days under usual use conditions.

Those fixing solutions having a composition generally employed in the art can be used in the present invention. Not only thiosulfates and thiocyanates but also organic sulfur compounds known as fixing agents can be used as fixing agents in the present invention.

Suitable preferred examples of fixing agents which can be used in the fixing solution include water-soluble thiosulfates such as sodium thiosulfate, potassium thiosulfate, ammonium thiosulfate, etc., water-soluble thiocyanates such as sodium thiocyanate, potassium thiocyanate, ammonium thiocyanate, etc., water-soluble organic diol fixing agents containing an oxygen atom or a sulfur atom such as 3-thia-1,5-pentanediol, 3,6-dithia-1,8-octanediol, 9-oxa-3,6,12,15-tetrathia-1,17-heptadecanediol, etc., water-soluble sulfur-containing organic dibasic acids and water-soluble salts thereof such as ethylenebisthioglycollic acid and the sodium salt thereof, etc., imidazolidinethiones such as methylimidazolidinethione, etc. Further, the fixing agents described in L. F. A. Mason, Photographic Processing Chemistry, pages 187 to 188, Focal Press (1966) are also preferred.

The following examples are given to illustrate the present invention in more detail.

EXAMPLE 1

An aqueous solution of silver nitrate and an aqueous solution of potassium bromide were added simultaneously to an aqueous solution of gelatin maintained at 50° C. over the course of 40 minutes. By maintaining the pAg at 7.9 during this time, a silver bromide emulsion having an average grain size of 0.22µ was prepared. Soluble salts were removed from the emulsion, and 48 mg, per mole of silver bromide, of sodium thiosulfate was added, and the mixture was chemically ripened at 60° C. for 60 minutes. The emulsion contained 120 g of gelatin per mole of silver bromide. The internal sensitivity of this emulsion was so low as to be negligible as compared with its surface sensitivity.

Compound (I-2) used in the present invention was added to the resulting silver bromide emulsion, and each of the compounds of the general formula (II) shown in Table 1 below was added in the amounts indicated. Furthermore, 2-hydroxy-4,6-dichloro-1,3,5-triazine sodium salt was added as a hardening agent. The resulting mixture was coated on a cellulose triacetate film so that the amount of silver was 40 mg per 100 cm².

For comparison, samples which contained a compound of the general formula (II) alone were also prepared.

Each of the samples was exposed for 1 second through an optical wedge, and developed for 5 minutes at 20° C. using a developer of the following formulation.

| Formulation of Developer | |
|---|---|
| N—Methyl-p-aminophenol Hemisulfate | 5 g |

| Formulation of Developer | |
|---|---|
| Hydroquinone | 10 g |
| Sodium Sulfite (anhydrous) | 75 g |
| Sodium Metaborate (tetrahydrate) | 30 g |
| 5-Methylbenzotriazole (1% methanol solution) | 30 ml |
| Potassium Hydroxide | 10 g |
| Water to make | 1 liter |
| pH | 11.1 |

After development, the sample was processed with a stopping bath of a 1.5 wt% aqueous solution of glacial acetic acid for 30 seconds at 20° C., a conventional fixing bath for 5 minutes at 20° C. and then washed.

The photographic characteristics of the samples obtained are shown in Table 1. The relative sensitivities shown in Table 1 are relative values of the reciprocals of the amounts of exposure required to give a density of 2.0 above fog, with the sensitivity value of Sample 1 taken as 100.

TABLE 1

| Sample No. | Amount of Compound (I-2) Added (mol/mol Ag) | Compound (II) Compound | Compound (II) Amount (mol/mol Ag) | $\gamma$ | Relative Sensitivity | Fog |
|---|---|---|---|---|---|---|
| 1 | — | — | — | 4.3 | 100 | 0.04 |
| 2 | $2.3 \times 10^{-2}$ | — | — | 10.5 | 170 | " |
| 3 | $2.3 \times 10^{-2}$ | II-3 | $1.3 \times 10^{-5}$ | 15 | 200 | " |
| 4 | " | " | $4.3 \times 10^{-4}$ | 19 | 190 | " |
| 5 | " | " | $1.3 \times 10^{-3}$ | " | 150 | " |
| 6 | " | " | $3.2 \times 10^{-3}$ | " | 140 | " |
| 7 | — | II-4 | $2.1 \times 10^{-4}$ | 4.3 | 95 | 0.06 |
| 8 | — | " | $6.4 \times 10^{-4}$ | 4.0 | 91 | " |
| 9 | $2.3 \times 10^{-2}$ | " | $2.1 \times 10^{-4}$ | 19 | 220 | " |
| 10 | " | " | $6.4 \times 10^{-4}$ | " | 200 | " |
| 11 | $2.3 \times 10^{-2}$ | II-26 | $1.9 \times 10^{-3}$ | 12 | 150 | 0.04 |
| 12 | " | " | $1.3 \times 10^{-2}$ | " | " | " |
| 13 | $2.3 \times 10^{-2}$ | II-7 | $2.1 \times 10^{-4}$ | 18 | 210 | " |
| 14 | " | " | $6.4 \times 10^{-4}$ | 16 | 210 | " |
| 15 | " | " | $1.9 \times 10^{-3}$ | 14 | 180 | " |
| 16 | $2.3 \times 10^{-2}$ | II-8 | $2.1 \times 10^{-4}$ | 17 | 210 | " |
| 17 | " | " | $6.4 \times 10^{-4}$ | " | 230 | " |
| 18 | " | " | $1.9 \times 10^{-3}$ | " | 245 | " |
| 19 | — | II-27 | $6.1 \times 10^{-5}$ | 4.3 | 48 | " |
| 20 | — | " | $1.8 \times 10^{-4}$ | 4.3 | 44 | " |
| 21 | $2.3 \times 10^{-2}$ | II-27 | $6.1 \times 10^{-5}$ | 14 | 170 | " |
| 22 | " | " | $1.8 \times 10^{-4}$ | " | " | " |
| 23 | " | " | $6.0 \times 10^{-4}$ | 15 | 165 | " |
| 24 | — | II-10 | $2.1 \times 10^{-4}$ | 3.8 | 85 | " |
| 25 | — | II-10 | $6.4 \times 10^{-4}$ | 3.8 | 83 | 0.04 |
| 26 | $2.3 \times 10^{-2}$ | " | $2.1 \times 10^{-4}$ | 18 | 245 | " |
| 27 | " | " | $6.4 \times 10^{-4}$ | " | 220 | " |
| 28 | " | " | $1.9 \times 10^{-3}$ | 16 | 200 | " |
| 29 | — | II-13 | $2.1 \times 10^{-4}$ | 3.8 | 91 | " |
| 30 | — | " | $6.4 \times 10^{-4}$ | 3.0 | 71 | " |
| 31 | $2.3 \times 10^{-2}$ | " | $2.1 \times 10^{-4}$ | 13 | 160 | 0.04 |
| 32 | " | " | $6.4 \times 10^{-4}$ | 18 | 150 | " |
| 33 | — | II-16 | $2.1 \times 10^{-4}$ | 4.3 | 62 | " |
| 34 | — | " | $6.4 \times 10^{-4}$ | 4.3 | 45 | " |
| 35 | $2.3 \times 10^{-2}$ | " | $2.1 \times 10^{-4}$ | 18 | 160 | " |
| 36 | " | " | $6.4 \times 10^{-4}$ | " | 150 | " |
| 37 | " | " | $1.9 \times 10^{-3}$ | " | " | " |
| 38 | $2.3 \times 10^{-2}$ | II-28 | $6.1 \times 10^{-5}$ | 15 | 180 | " |
| 39 | " | " | $1.8 \times 10^{-4}$ | " | " | " |
| 40 | " | " | $6.0 \times 10^{-4}$ | 14 | 185 | " |
| 41 | — | II-5 | $1.4 \times 10^{-5}$ | 4.0 | 83 | 0.06 |
| 42 | — | " | $4.3 \times 10^{-5}$ | 3.7 | 66 | " |
| 43 | $2.3 \times 10^{-2}$ | " | $1.4 \times 10^{-5}$ | >20 | 300 | " |
| 44 | " | " | $4.3 \times 10^{-5}$ | " | 320 | " |
| 45 | " | " | $1.4 \times 10^{-4}$ | " | 270 | " |
| 46 | — | II-14 | $1.1 \times 10^{-4}$ | 4.0 | 60 | 0.05 |
| 47 | — | II-14 | $4.3 \times 10^{-4}$ | 4.3 | 47 | 0.05 |
| 48 | $2.3 \times 10^{-2}$ | " | $1.1 \times 10^{-4}$ | 17 | 250 | " |
| 49 | " | " | $4.3 \times 10^{-4}$ | 20 | 300 | " |
| 50 | — | II-24 | $6.1 \times 10^{-5}$ | 4.3 | 42 | 0.04 |
| 51 | — | " | $1.8 \times 10^{-4}$ | 3.0 | 32 | " |
| 52 | $2.3 \times 10^{-2}$ | " | $6.1 \times 10^{-5}$ | 16 | 120 | " |
| 53 | " | " | $1.8 \times 10^{-4}$ | " | 110 | " |
| 54 | — | II-17 | $1.1 \times 10^{-4}$ | 4.2 | 47 | " |
| 55 | — | " | $4.3 \times 10^{-4}$ | 4.0 | 15 | " |
| 56 | $2.3 \times 10^{-2}$ | " | $1.1 \times 10^{-4}$ | 18 | 120 | " |
| 57 | " | " | $4.3 \times 10^{-4}$ | 18 | 120 | " |
| 58 | " | II-29 | $6.1 \times 10^{-5}$ | 14 | 175 | " |
| 59 | " | " | $1.8 \times 10^{-4}$ | 16 | " | " |
| 60 | " | " | $6.0 \times 10^{-4}$ | " | 200 | " |
| 61 | — | II-18 | $6.1 \times 10^{-5}$ | 2.3 | 15 | " |
| 62 | — | " | $1.8 \times 10^{-4}$ | 2.0 | 7 | " |
| 63 | $2.3 \times 10^{-2}$ | II-18 | $6.1 \times 10^{-5}$ | 16 | 170 | " |
| 64 | " | " | $1.8 \times 10^{-4}$ | " | 150 | " |
| 65 | " | " | $6.0 \times 10^{-4}$ | 18 | 145 | " |

TABLE 1-continued

| Sample No. | Amount of Compound (I-2) Added (mol/mol Ag) | Compound (II) Compound | Compound (II) Amount (mol/mol Ag) | $\gamma$ | Relative Sensitivity | Fog |
|---|---|---|---|---|---|---|
| 66 | $2.3 \times 10^{-2}$ | II-19 | $6.1 \times 10^{-5}$ | 15 | 170 | 0.04 |
| 67 | " | " | $1.8 \times 10^{-4}$ | 16 | " | " |
| 68 | " | " | $6.0 \times 10^{-4}$ | " | 175 | " |
| 69 | $2.3 \times 10^{-2}$ | II-21 | $6.1 \times 10^{-5}$ | 14 | 180 | " |
| 70 | $2.3 \times 10^{-2}$ | II-25 | $6.1 \times 10^{-5}$ | 14 | 180 | " |
| 71 | " | " | $1.8 \times 10^{-4}$ | " | " | " |
| 72 | " | II-22 | $6.1 \times 10^{-5}$ | 14 | 180 | " |
| 73 | " | " | $1.8 \times 10^{-4}$ | 16 | 160 | " |

The results in Table 1 above show that the combined use of the compounds of the general formulae (I) and (II) gives rise to a marked increase in gamma in comparison with the use of the compound of the general formula (I) or (II) alone. In some cases, the sensitivity increased as the gamma increased.

EXAMPLE 2

Each of Sample No. 1 (which did not contain Compound (I-2)) and Sample No. 2 (which contained Compound (I-2) in an amount of $2.3 \times 10^{-2}$ mole/mole Ag) was exposed for 1 second through an optical wedge, and then developed at 20° C. for 5 minutes with a developer having the same composition as described in Example 1 to which each of Compounds (II-14), (II-5), (II-18), (II-17) and (II-25) had been added as a methanol solution in the amounts shown in Table 2 below.

After development, each sample was processed with a stopping bath of a 1.5 wt% aqueous solution of glacial acetic acid for 30 seconds at 20° C., a conventional fixing bath for 5 minutes at 20° C. and then washed.

TABLE 2

| Sample No. (as in Example 1) | Compound (II) in Developer Compound | Compound (II) in Developer Amount (mol/l) | $\gamma$ | Relative Sensitivity | Fog |
|---|---|---|---|---|---|
| 1 | — | — | 4.3 | 100 | 0.04 |
| 2 | — | — | 10.5 | 170 | " |
| 1 | II-14 | $2.3 \times 10^{-4}$ | 4.0 | 98 | 0.05 |
| 2 | " | " | 13 | 200 | " |
| 2 | " | $1.2 \times 10^{-3}$ | 15 | 220 | " |
| 2 | " | $2.1 \times 10^{-3}$ | 15 | 280 | " |
| 1 | II-5 | $9 \times 10^{-6}$ | 4.3 | 90 | 0.05 |
| 2 | " | " | 13 | 180 | " |
| 2 | " | $2.7 \times 10^{5}$ | 15 | 210 | " |
| 2 | " | $9 \times 10^{-5}$ | 14 | 240 | " |
| 1 | II-18 | $6 \times 10^{-4}$ | 4.0 | 90 | 0.04 |
| 2 | " | " | 13 | 180 | " |
| 1 | II-17 | $6 \times 10^{-4}$ | 4.0 | 96 | " |
| 2 | " | " | 14 | 210 | " |
| 1 | II-25 | $6 \times 10^{-4}$ | 4.0 | 100 | " |
| 2 | " | " | 13 | 190 | " |

As can be seen from the results in Table 2, high gamma and sensitivity can be obtained without any appreciable increase in fog even when the photographic material containing Compound (I-2) is developed using a developer containing a compound of the general formula (II).

EXAMPLE 3

To the same type of silver bromide emulsion as described in Example 1 was added each of Compounds (I-18), (I-1), (I-7) and (I-17) in the amounts shown in Table 3 below, and in the same way as in Example 1, Samples 76, 78, 80 and 82 were prepared. Moreover, samples containing Compound (II-5) in an amount of $2.1 \times 10^{-5}$ mole/mole Ag (Samples 77, 79, 81, and 83), a sample containing only Compound (II-5) (Sample 75), and a sample which did not contain a compound of the general formula (I) nor Compound II-5 (Sample 74) were prepared.

Each of these samples was exposed for 1 second through an optical wedge, and then developed at 20° C. for 5 minutes with a developer of the following formulation.

| Formulation of Developer | |
|---|---|
| N—Methyl-p-aminophenol Hemisulfate | 5 g |
| Hydroquinone | 10 g |
| Sofium Sulfite (anhydrous) | 75 g |
| Sodium Metaborate (tetrahydrate) | 30 g |
| 5-Methylbenzotriazole (1% methanol solution) | 30 ml |
| Potassium Hydroxide | 12 g |
| Water to make | 1 liter |

After development, each sample was processed with a stopping bath of a 1.5 wt% aqueous solution of glacial acetic acid for 30 seconds at 20° C., a conventional fixing bath for 5 minutes at 20° C. and then washed.

The photographic characteristics are shown in Table 3 below.

TABLE 3

| Sample No. | Compound (I) Compound | Compound (I) Amount (mol/mol Ag) | Compound (II) Compound | Compound (II) Amount (mol/mol Ag) | $\gamma$ | Relative Sensitivity | Fog |
|---|---|---|---|---|---|---|---|
| 74 | — | — | — | — | 4.5 | 100 | 0.04 |
| 75 | — | — | II-5 | $2.1 \times 10^{-5}$ | 3.5 | 75 | 0.06 |
| 76 | I-18 | $4.5 \times 10^{-2}$ | — | — | 8 | 130 | 0.04 |
| 77 | " | " | II-5 | $2.1 \times 10^{-5}$ | 13 | 250 | 0.06 |
| 78 | I-1 | $2.5 \times 10^{-2}$ | — | — | 10 | 155 | 0.04 |
| 79 | " | " | II-5 | $2.1 \times 10^{-5}$ | 16 | 280 | 0.08 |
| 80 | I-7 | $5.9 \times 10^{-2}$ | — | — | 7 | 120 | 0.04 |
| 81 | " | " | II-5 | $2.1 \times 10^{-5}$ | 11 | 220 | 0.05 |
| 82 | I-17 | $6.9 \times 10^{-3}$ | — | — | 15 | 190 | 0.06 |
| 83 | " | " | II-5 | $2.1 \times 10^{-5}$ | 18 | 350 | 0.10 |

As can be seen from the results in Table 3, when Compound (II-5) is used in combination with each of Compounds (I-18), (I-1), (I-7) and (I-17), a higher gamma and a higher sensitivity are obtained than in the case of using each of the compounds alone, as in Example 1.

While the invention has been described in detail and with reference to specific embodiments thereof, it will be apparent to one skilled in the art that various changes and modifications can be made therein without departing from the spirit and scope thereof.

What is claimed is:

1. A method for forming a high contrast negative photographic image, which comprises imagewise exposing a photographic material comprising a support having thereon at least one photographic silver halide emulsion layer comprising substantially surface latent image type silver halide with the photographic silver halide emulsion layer or at least one hydrophilic colloid layer of the photographic material containing a compound of general formula [I]

wherein $R^1$ represents an aryl group and $R^2$ represents a hydrogen atom, a phenyl group or an unsubstituted alkyl group containing 1 to 3 carbon atoms, wherein the compound of general formula [I] is present in an amount of about $10^{-6}$ to $10^{-1}$ mole per mole of silver halide and a hydroquinone compound of the general formula [II]

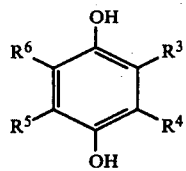

wherein $R^3$, $R^4$, $R^5$ and $R^6$, which may be the same or different, each represents a hydrogen atom, a sulfo group, an alkyl group, an aryl group, an aralkyl group, a heterocyclic group or a group of the formula —O—$R^7$ or —S—$R^7$, where $R^7$ represents an alkyl group, an aryl group, an aralkyl group or a heterocyclic group, and wherein at least one or $R^3$, $R^4$, $R^5$ and $R^6$ represents an —S—$R^7$ group, the amount of the compound of the general formula [II] in the photographic material being about $5\times10^{-7}$ to $5\times10^{-2}$ mole per mole of the silver halide, and then developing the imagewise exposed material with a developing agent consisting essentially of a member selected from the group consisting of an aminophenol, a 3-pyrazolidone, a 1-phenyl-3-pyrazoline or hydroquinone.

2. The method of claim 1, wherein $R^2$ represents a hydrogen atom, a methyl group or a phenyl group.

3. The method of claim 1, wherein $R^1$ represents an unsubstituted phenyl group or a tolyl group, and $R^2$ represents a hydrogen atom or a methyl group.

4. The method of claim 1, wherein at least one of $R^3$, $R^4$, $R^5$ and $R^6$ represents a group of the formula —S—$R^7$ in which $R^7$ represents a heterocyclic group.

5. The method of claim 1, wherein the compound of the the general formula [II] is present in the silver halide emulsion layer or in at least one hydrophilic colloid layer in an amount of about $5\times10^{-7}$ to $5\times10^{-2}$ mole/mole Ag.

6. The method of claim 1, wherein the developing is by using a developer which contains at least 0.15 mole/liter of sulfite ion.

7. The method of claim 1, wherein the silver halide emulsion layer contains a binder, and said binder is present in an amount of about 250 g or less of binder, per mole of the silver halide.

8. The method of claim 1, wherein said high contrast negative photographic image is a black and white negative photographic image.

9. The method of claim 1, wherein said developing is with a developer free of ascorbic acid.

10. The method of claim 1, wherein said contrast is to a level of γ more than 8.

11. The method of claim 1, wherein said compound of the general formula [I] and said compound of the general formula [II] do not serve as developing agents but rather serve to increase sensitivity and contrast.

12. The method of claim 1, wherein the silver halide is at least one of a silver chlorobromide containing about 80 mole% or less of silver chloride, silver bromide, a silver iodobromide containing about 10 mole% or less of silver iodide, and silver iodobromochloride.

* * * * *